(12) United States Patent
Sloushch et al.

(10) Patent No.: US 11,845,440 B2
(45) Date of Patent: Dec. 19, 2023

(54) CONTACTLESS DETECTION AND MONITORING SYSTEM OF VITAL SIGNS OF VEHICLE OCCUPANTS

(71) Applicant: Red Bend Ltd., Hod Ha'Sharon (IL)

(72) Inventors: Ilya Sloushch, Netanya (IL); Vadim Kotlar, Haifa (IL); Konstantin Berezin, Netanya (IL); Alex Arshavski, Netanya (IL)

(73) Assignee: RED BEND LTD., Hod Ha'sharon (IL)

( * ) Notice: Subject to any disclaimer, the term of this patent is extended or adjusted under 35 U.S.C. 154(b) by 665 days.

(21) Appl. No.: 16/635,198

(22) PCT Filed: Aug. 1, 2018

(86) PCT No.: PCT/IL2018/050856
§ 371 (c)(1),
(2) Date: Jan. 30, 2020

(87) PCT Pub. No.: WO2019/026076
PCT Pub. Date: Feb. 7, 2019

(65) Prior Publication Data
US 2020/0317207 A1 Oct. 8, 2020

Related U.S. Application Data

(60) Provisional application No. 62/540,083, filed on Aug. 2, 2017.

(51) Int. Cl.
*B60W 40/08* (2012.01)
*A61B 5/0205* (2006.01)
(Continued)

(52) U.S. Cl.
CPC .......... *B60W 40/08* (2013.01); *A61B 5/0205* (2013.01); *G01S 13/53* (2013.01); *G01S 13/88* (2013.01);
(Continued)

(58) Field of Classification Search
USPC .......................................... 342/84
See application file for complete search history.

(56) References Cited

U.S. PATENT DOCUMENTS 5,573,012 A * 11/1996 McEwan ................ A61B 5/024
600/595
6,820,897 B2 11/2004 Breed et al.
(Continued)

FOREIGN PATENT DOCUMENTS

CN 102542619 A 7/2012
CN 106068097 A 11/2016
(Continued)

OTHER PUBLICATIONS

Https://www.hopkinsmedicine.org/health/conditions-and-diseases/vital-signs-body-temperature-pulse-rate-respiration-rate-blood-pressure#:#:text=Vital%20signs%20are%20measurements%20of,Respiration%20rate%20(rate%20of%20breathing).*
(Continued)

*Primary Examiner* — Jonathan M Dager
(74) *Attorney, Agent, or Firm* — McCoy Russell LLP

(57) ABSTRACT

Disclosed are methods and systems for detecting vital signs of occupants in vehicles, for example, the vehicle cabin. A signal unit transmits a radar signal to the occupant and receiving the radar signal reflected from the occupant. The reflected radar signal is analyzed with respect to vibration data of the vehicle, to produce a modified signal. The modified signal is analyzed to determine the vital signs of the occupant.

20 Claims, 13 Drawing Sheets

(51) Int. Cl.
   *G01S 13/53*  (2006.01)
   *G01S 13/88*  (2006.01)

(52) U.S. Cl.
   CPC .......... *B60W 2040/0872* (2013.01); *B60W 2520/105* (2013.01); *B60W 2540/049* (2020.02); *B60W 2540/221* (2020.02)

(56) References Cited

U.S. PATENT DOCUMENTS

| | | | | |
|---|---|---|---|---|
| 7,760,130 | B2* | 7/2010 | Antonsson | G01S 13/18 342/134 |
| 8,454,528 | B2* | 6/2013 | Yuen | A61B 5/0205 600/407 |
| 8,597,196 | B2 | 12/2013 | Kishi et al. | |
| 8,725,311 | B1* | 5/2014 | Breed | A61B 5/11 701/1 |
| 9,492,099 | B2* | 11/2016 | Gamble | A61B 5/0507 |
| 9,671,492 | B2 | 6/2017 | Diewald | |
| 9,791,551 | B1* | 10/2017 | Eshraghi | G01S 7/0232 |
| 9,848,814 | B2* | 12/2017 | Benson | B60N 2/5678 |
| 9,862,271 | B2* | 1/2018 | Branković | A61B 5/6893 |
| 10,201,278 | B2* | 2/2019 | Lux | A61B 5/024 |
| 10,227,054 | B2* | 3/2019 | Diewald | G01S 7/414 |
| 10,473,762 | B2* | 11/2019 | Lilja | G01S 7/415 |
| 10,499,856 | B2* | 12/2019 | Fung et al. | G08C 17/02 |
| 10,576,988 | B2* | 3/2020 | Kim | G08B 31/00 |
| 10,810,411 | B2* | 10/2020 | Tai | H03B 21/02 |
| 10,859,675 | B2* | 12/2020 | McMahon | G01S 13/62 |
| 11,054,511 | B2* | 7/2021 | Shamain | H04B 1/69 |
| 11,378,671 | B1* | 7/2022 | El Dokor | G01S 13/56 |
| 2002/0140214 | A1* | 10/2002 | Breed | G01S 15/88 280/735 |
| 2005/0073424 | A1* | 4/2005 | Ruoss | A61B 5/18 342/61 |
| 2009/0278728 | A1* | 11/2009 | Morgan | G01S 13/88 342/115 |
| 2010/0056937 | A1* | 3/2010 | Imamura | B60N 2/002 600/509 |
| 2014/0039330 | A1* | 2/2014 | Seo | A61B 5/02255 600/509 |
| 2014/0058254 | A1 | 2/2014 | Yamaji | |
| 2014/0221781 | A1 | 8/2014 | Schrauf et al. | |
| 2015/0126818 | A1* | 5/2015 | Fung | A61B 5/02405 600/300 |
| 2015/0313475 | A1* | 11/2015 | Benson | A61B 5/14552 600/323 |
| 2016/0054438 | A1* | 2/2016 | Patole | G01S 7/35 342/127 |
| 2016/0200276 | A1* | 7/2016 | Diewald | G01S 13/04 342/28 |
| 2016/0259037 | A1* | 9/2016 | Molchanov | G01S 7/0233 |
| 2016/0354027 | A1* | 12/2016 | Benson | A61B 5/0533 |
| 2017/0097413 | A1* | 4/2017 | Gillian | G01S 13/88 |
| 2017/0143253 | A1* | 5/2017 | Krenzer | A61B 5/4809 |
| 2017/0282828 | A1* | 10/2017 | Carenza | G01S 7/415 |
| 2017/0296128 | A1* | 10/2017 | Aoki | A61B 5/024 |
| 2017/0347961 | A1* | 12/2017 | Perraut | A61B 5/6893 |
| 2018/0022358 | A1* | 1/2018 | Fung | G06V 40/70 701/36 |
| 2018/0081030 | A1* | 3/2018 | McMahon | G01S 7/415 |
| 2018/0170213 | A1 | 6/2018 | Lu-Dac et al. | |
| 2018/0229674 | A1* | 8/2018 | Heinrich | B60K 28/063 |
| 2018/0263502 | A1* | 9/2018 | Lin | G01S 7/415 |
| 2019/0094355 | A1 | 3/2019 | Nakagawa | |
| 2019/0117144 | A1 | 4/2019 | Benninger et al. | |
| 2020/0383580 | A1* | 12/2020 | Shouldice | A61B 5/0816 |
| 2021/0055137 | A1* | 2/2021 | An | G01D 11/10 |
| 2021/0128068 | A1* | 5/2021 | Ghoshal | A61B 5/0507 |
| 2021/0190902 | A1* | 6/2021 | Amihood | G01S 7/358 |
| 2022/0039718 | A1* | 2/2022 | Kowata | B60N 2/66 |
| 2022/0188555 | A1* | 6/2022 | Park | G02B 27/54 |
| 2023/0045261 | A1* | 2/2023 | Ozawa | A61B 5/02444 |

FOREIGN PATENT DOCUMENTS

| | | |
|---|---|---|
| DE | 102016213077 A1 | 1/2018 |
| DE | 102017216239 A1 | 3/2019 |
| JP | 2013153782 A | 8/2013 |
| JP | 2014039666 A | 3/2014 |
| JP | 2016220816 A | 12/2016 |
| JP | 2017012650 A | 1/2017 |
| JP | 2017104360 A | 6/2017 |
| WO | 2012115220 A1 | 8/2012 |
| WO | 2016038148 A1 | 3/2016 |

OTHER PUBLICATIONS

International Search Report of PCT/IL2018/050856 dated Nov. 12, 2018.
Search Report of European Application No. 18841275.3 dated Jun. 25, 2020.
Office Action of Chinese Application No. 201880049998.0 dated Jan. 15, 2022.
English translation of Office Action of Chinese Application No. 201880049998.0 dated Jan. 15, 2022.
English translation of Office Action of Japanese Application No. 2020-503923 dated Jan. 18, 2022.
Office Action of Indian Application No. 202017008013 dated Feb. 23, 2022.

* cited by examiner

CONTACTLESS DETECTION AND MONITORING SYSTEM OF VITAL SIGNS OF VEHICLE OCCUPANTS

CROSS REFERENCES TO RELATED APPLICATIONS

This application is related to and claims priority from commonly owned U.S. Provisional Patent Application Ser. No. 62/540,083, entitled: Contactless Detection and Monitoring System of Vital Signs of Vehicle Occupants, filed on Aug. 2, 2017, the disclosure of which is incorporated by reference in its entirety herein.

TECHNICAL FIELD

The present invention relates to systems and methods for monitoring and detecting vehicle occupants and their vital signs.

BACKGROUND OF THE INVENTION

Technologies which operates by weight or pressure sensing, acoustic radar (occupancy sensor), radio frequency (RF) radars, 2D- and 3D-imaging, and thermal imaging, have been used to detect vehicle occupants seat occupancy monitoring for seat belt remainders, and infant detection, for forgotten/left infants in vehicles.

SUMMARY OF THE INVENTION

The present invention is directed to systems and methods for detecting vital signs of motor vehicle occupants, such as the occupants in the vehicle cabin, in dynamic environments. The detecting is performed, for example, by using radio frequency (RF) radar, to detect vital signs, based on the radar-based detection and monitoring of, for example, one or more of: respiratory or breathing rates (RR), heart rate (HR), hart rate variability (HRV) and speech state recognition. The detection of vital signs is also used to determine the presence of an occupant in the vehicle and/or the number of occupants in the vehicle, regardless of the occupant's location in the vehicle. Additionally, the present invention is that the system detects vehicle occupants out of position (OOP). Should such an OOP detection be made, this may indicate a vehicle accident, or an incapacitated occupant.

The present invention discloses methods and systems for detecting vital signs of occupants in vehicles, for example, the vehicle cabin. A signal unit transmits a radar signal to the occupant and receiving the radar signal reflected from the occupant. The reflected radar signal is analyzed with respect to vibration data of the vehicle, to produce a modified signal. The modified signal is analyzed to determine the vital signs of the occupant.

The present invention is directed to detecting vital signs, for example, breathing or respiratory rate, heart rate, and heart rate variability, of vehicle cabin occupants from the seats of the vehicle cabin.

The present invention is directed to signal units with multiple paths for the received radar signals, and each of the paths has its own analog amplification and filtering (levels/edges) which are adjusted based on the driving conditions (e.g., vibrations associated with the movement of the vehicle).

The present invention is such that the system monitors the vital signs of the driver of the vehicle during driving.

The present invention detects occupant vital signs and based on the vital signs detects driver conditions such as driver drowsiness, falling asleep and the like.

The present invention is such that the sensor units thereof may be located on the vehicle dashboard or integrated into it. The sensor units define a system, which may be independent of the vehicle's systems or can be integrated into the vehicle's systems.

Embodiments of the invention are directed to a method for determining the vital signs of an occupant in a vehicle. The method comprises: transmitting a radar signal to the occupant and receiving the radar signal reflected from the occupant; analyzing the reflected radar signal with respect to vibration data of the vehicle to produce a modified signal: and, analyzing the modified signal to determine the vital signs of the occupant.

Optionally, the method is such that the vital signs include one or more of breathing rate, heart rate and heart rate variability.

Optionally, the method is such that the radar signal is from Doppler radar.

Optionally, the method is such that the reflected signal is obtained in analog form and is converted to a digital form, and the modified signal includes a modified digital signal.

Optionally, the method is such that the vital sign to be measured is breathing rate of the occupant and the radar signal reflected from the occupant results in a signal based on breathing rate harmonics.

Optionally, the method is such that the vital sign to be monitored includes heart rate.

Optionally, the method is such that heart rate is determined by processes including: obtaining the modified signal; dividing the modified signal into segments, each segment corresponding to a frequency, analyzing a plurality of peaks of the segment for harmonics, including, for each peak; applying weight factors to each of the harmonics; accumulate the energy from the harmonics as multiplied by the weight factors; and, determining the peak with the highest accumulated energy.

Optionally, the method is such that the peak determined to have the highest accumulated energy corresponds to the heart rate.

Optionally, the method is such that the determining heart rate variability includes the processes of: obtaining the modified signal; determine the artifacts in the modified signal; analyzing the modified signal for consecutive peaks between the artifacts; and, determining a portion of the modified signal with at least a predetermined number of consecutive peaks; and, calculating the heart rate variability parameters from the modified signal with at least a predetermined number of consecutive peaks.

Optionally, the method is such that it additionally comprises: dividing the reflected signal into a first pathway for respiration rate frequencies and a second pathway for the heart rate frequencies, prior to the analyzing of the reflected signal.

Embodiments of the invention are directed to a method of decreasing the impact of movement by a subject on the heart rate measurements for the subject, by filtering the heart rate fundamental frequency and determining the signal by analyzing the signal harmonics.

Embodiments of the invention are directed to a method of decreasing the impact of movement by a subject on the heart rate measurements by focusing proximately positioned radar at the aorta area.

Embodiments of the invention are directed to a method of decreasing the impact of movement by a subject on the breathing rate measurements by focusing proximately positioned radar at the diaphragm area.

Optionally, the method of decreasing the impact of movement by a subject on the breathing rate measurements is such that the aorta area is between the L1 and L5 vertebrae.

Optionally, the method of decreasing the impact of movement by a subject on the breathing rate measurements is such the vibration data is obtained from an inertial measurement unit.

Embodiments of the invention are directed to a system for determining the vital signs of a subject. The system comprises: a radar transceiver for transmitting a signal to the subject and receiving the signal reflected from the subject; a signal converter for converting the reflected signal to a converted signal for processing by a processor; a vibration detection unit for detecting vibrations local to the subject and providing data representative of the local vibrations; and, a processor in electronic communication with the signal converter and the vibration detection unit, programmed to: a) analyze the converted signal with respect to vibration data, to produce a modified signal, and b) analyze the modified signal to determine the vital signs of the occupant.

Optionally, the system is such that the processor programmed to analyze the modified signal to determine the vital signs of the occupant, determines the vital signs including one or more of breathing rate, heart rate, and heart rate variability.

Optionally, the system is such that the vibration detection unit includes and inertial measurement unit (IMU).

Optionally, the system is such that the signal converter includes an analog to digital converter (ADC).

Optionally, the system is such that it additionally comprises: a filtration and amplification circuit in electronic communication with the radar transceiver and the signal converter, including two passband pathways for separating respiratory rate frequencies and heart rate frequencies of the reflected signal.

Optionally, the system is such that the radar transceiver, the signal converter, the processor and the vibration detection unit define a single sensor unit.

Embodiments of the invention are directed to determining a vehicle occupant based on vital signs. The method comprises: transmitting a radar signal to vehicle cabin and receiving the reflected signal; analyzing the reflected signal with respect to vibration data of the vehicle to produce a modified signal: and, analyzing the modified signal to determine the presence of vital signs in the vehicle cabin; and, should the vital signs be present, an occupant has been detected in the vehicle cabin.

Embodiments of the invention are directed to a method for determining the minimum gain level in a filtering and amplification circuit. The method comprises: generating a harmonic waveform; transmitting the waveform and receiving the reflected waveform; and, modifying the gain level of an amplifier in the filtering and amplification circuit to detect the reflected waveform.

Optionally, the method is such that it is performed in a vehicle cabin.

Optionally, the method is such that the vehicle cabin is empty of occupants.

Embodiments of the invention are directed to a method for determining the number of occupants in a vehicle. The method comprises: transmitting a radar signal into the vehicle cabin, and receiving the radar signal reflected from one or more occupants; analyzing the reflected radar signal with respect to vibration data of the vehicle to produce a modified signal: analyzing the modified signal to determine vital signs of the occupants; and, based on the number of vital signs detected, determining the number of occupants in the vehicle cabin.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings.

DETAILED DESCRIPTION OF THE DRAWINGS

Figure 1A:
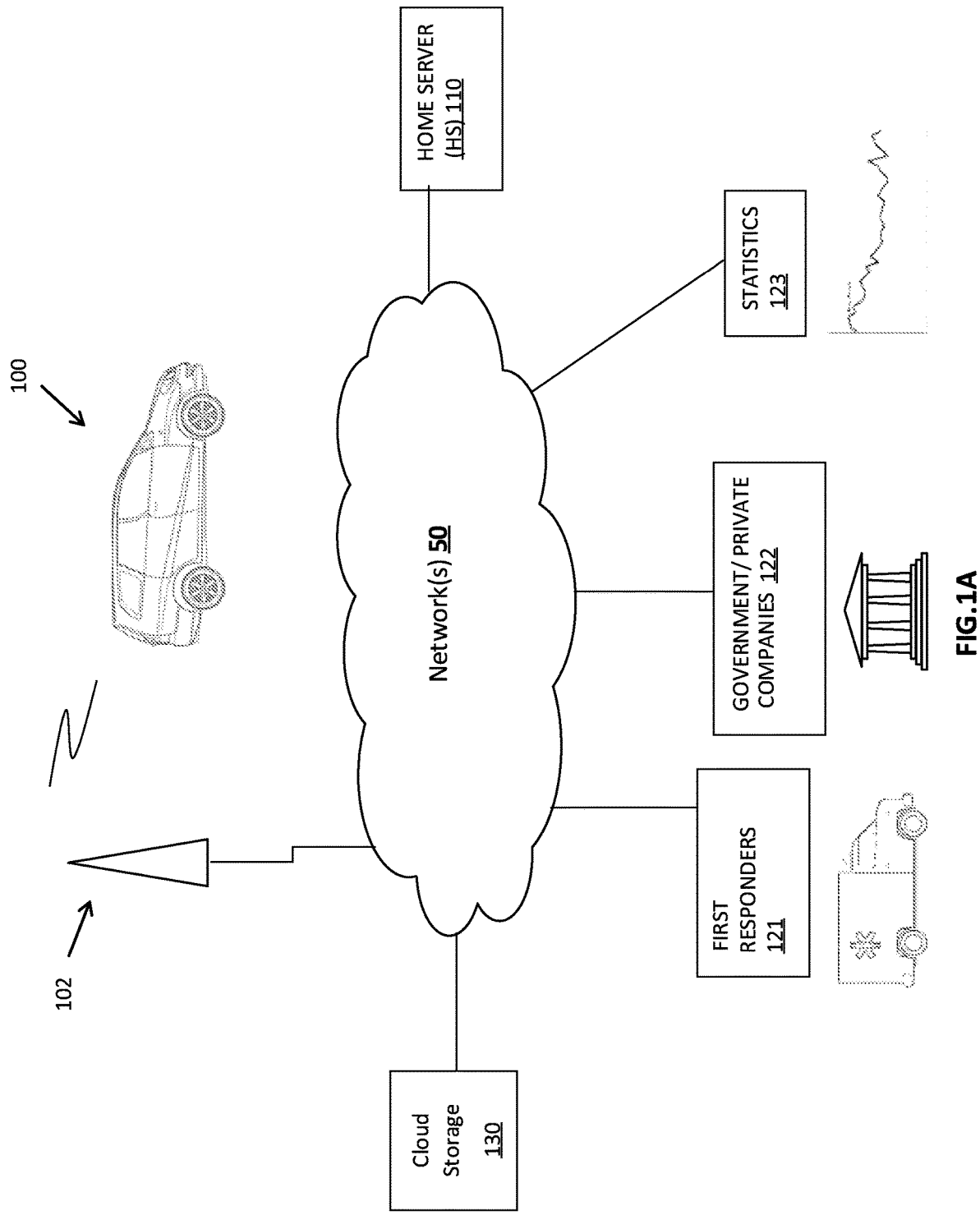
FIG. 1A is a diagram of an environment in which embodiments of the present invention operate.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more non-transitory computer readable (storage) medium(s) having computer readable program code embodied thereon.

Throughout this document, numerous textual and graphical references are made to trademarks. These trademarks are the property of their respective owners, and are referenced only for explanation purposes herein.

The invention includes a system comprising sensor units, which include RF radar transceivers, including one or more antennas, which are connected with Transmit (TX) and Receiver (RX) blocks. TX power, operation frequency, waveform and RX Gain are configured by control signals, which come from Digital to Analog Converters (DACs) and Power supply voltages. The RX block (blocks) includes down-converters to intermediate frequency (IF) outputs. The RF radar transceiver is coupled to an amplifying and filtering analog circuit or block. The gain and the IF pass band of the analog block are configured by corresponding control signals, which originate from dedicated DACs. Outputs (output) of the analog block are connected to inputs of Analog to Digital Converter (ADC), having a digital interface with the central processing unit (CPU).

The system may have an Inertial Measurement Unit (IMU), for acceleration and/or angle measurements which will affect amplification levels and filtering edges. The IMU is used to monitor the vibration level of the dynamic environment, for example, the vehicle vibrations resulting from travel over roads, such as highways, off-road trails, surface streets, various road pavings (even and uneven surfaces), turns, internal and external noises.

The CPU is also connected with DACs, as well as other sensors (for example, mechanical vibration, temperature, doors and motor state of the vehicle). Functions of the CPU, include, for example, the calibration of RF transceiver and the analog blocks, and storage calibrated parameters, the detection of desired signals from the objects that relate to respiration and heartbeat, by optimal digital filtering of main harmonics of corresponding signals, using weight coefficients for each harmonic, which takes into account different interferences, such as movement of the objects, object speaking, and the like, detection of the signal parameters from objects related to the occupation status, using adaptive signal thresholds, which takes into account calibration factors and relationships between signals, which are received from different antennas.

The RF radar is, for example, Doppler radar, and operates in one or more modulations including, for example, continuous waveform (CW), FM/PM/AM/Pulse modulations.

During operation of the system, the RF radar transceiver generates radio waves, which propagate from the radar transmission antenna to the objects. The signals are reflected from the object and collected by receiver antenna(s) of the RF radar modules.

The receiving signal after a digitization is received by the CPU, which applies algorithms to process these received and now digital signals. The processing also accounts for vehicle parameters, such as those for vibrations, when determining breathing rates, heart rates, heart rate variabilities and driver activity, or vehicle cabin occupants.

Figure 4A:
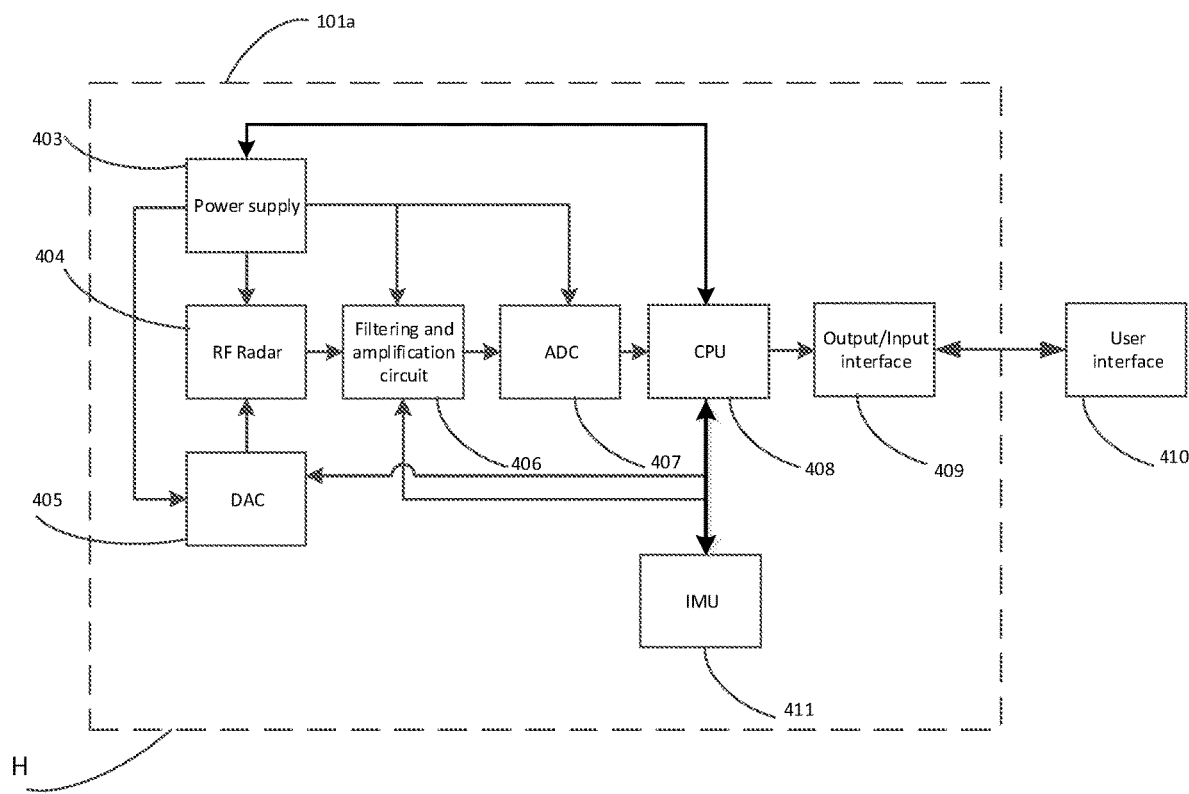
FIG. 4A is a diagram of a sensor unit and processing system in accordance with embodiments of the present invention.

The present invention is directed to a contactless detection and monitoring system of vital signs of vehicle occupants, which uses RF (Radio Frequency) radar to detect human or animal body vibrations/oscillations, relative to that vibration/oscillations calculations made by the system for heart rate and respiratory rate. FIG. 1A shows an exemplary environment for the invention. Within a vehicle 100 are apparatus 101, known hereinafter as sensor units 101a-101i (FIG. 1B), which include, for example, radar transceivers 404 (FIG. 4A). These sensor units 100a-100i are linked to a network(s) 50, for example, via a cellular tower 102, WiFi® or the like, so as to be linked to a home server (HS) 110, or main server, which together with the sensor units 101a-101i forms a system. Via the network(s) 50, the home server 110 is linked to a multitude of other servers, devices, and the like, such as servers associated with first responders 121, e.g., police, fire, ambulances, government 122 and governmental agencies authorities, and the like, statistical organizations 123, and storage media 130, such as cloud storage.

The network 50 of FIG. 1A is, for example, a communications network, such as Bluetooth®, Zigbee, Zwave, LORA, V2X, and a Local Area Network (LAN), or a Wide Area Network (WAN), including public networks such as the Internet. The network 50, although shown as a single network, may be a combination of networks and/or multiple networks including, for example, in addition to the Internet, one or more cellular networks, wide area networks (WAN), and the like. "Linked" as used herein includes both wired or wireless links, either direct or indirect, and placing the computers, including, servers, components and the like, in electronic and/or data communications with each other.

Figure 1B:
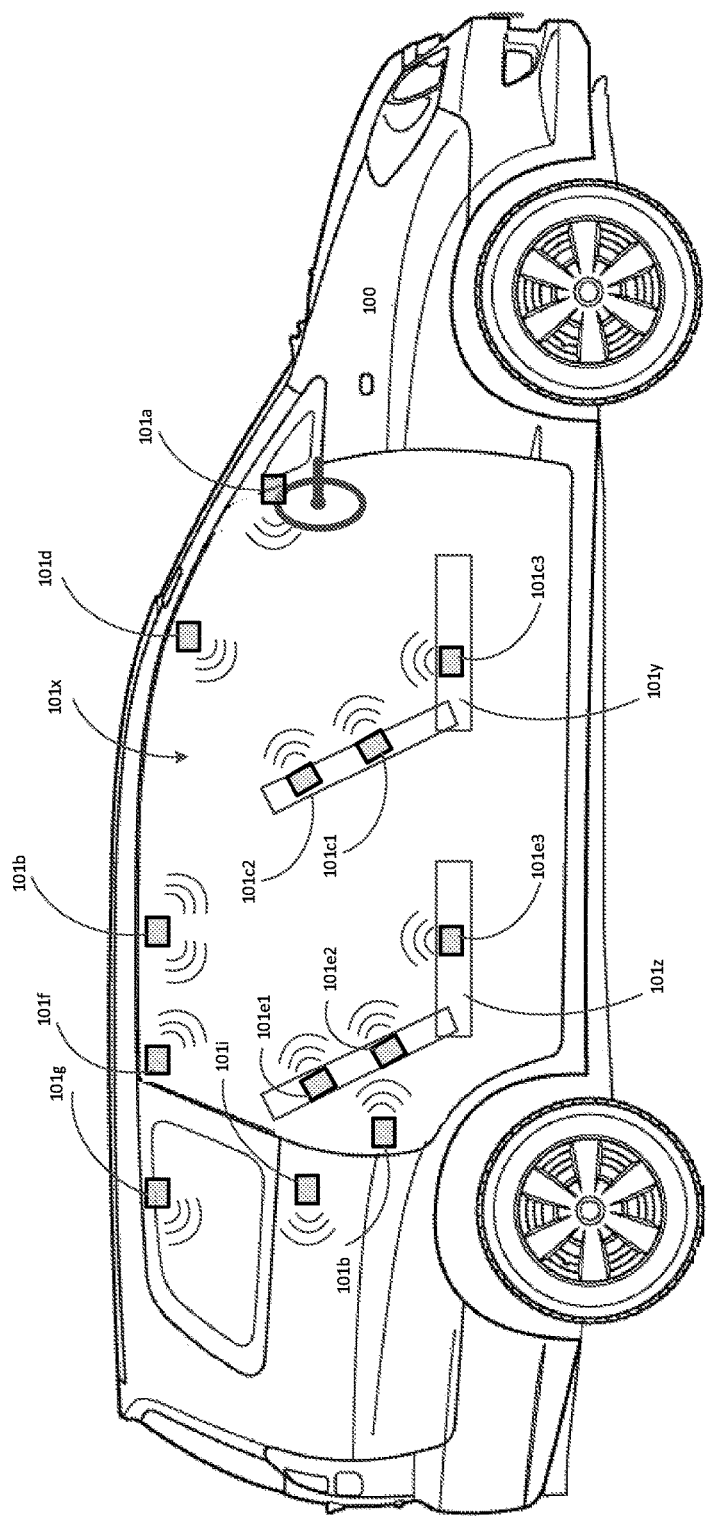
FIG. 1B is a diagram of the system of invention in a vehicle.

Turning to FIG. 1B, the vehicle 100, for example, the cabin 101x of the vehicle 100 includes sensor units 101a-101i therein. The sensor units 101a-101i are mounted, for example, on the vehicle dashboard 101a, on the ceiling 101b, 101f, 101g, within seats 101c1-101c3, 101e1-101e3, rear view mirror 101d, behind the seats 101h, the trunk 101i or baggage compartment, and the like. The sensor units 101a-101i are spaced in the vehicle cabin 101x to provide coverage of the entire vehicle cabin 101x. Each of the sensor units 101a-101i is typically used for providing specific applications for each of the various occupants. For example, seat mounted sensor units 101c1 to 101c3 and 101e1 to 101e3 are used in detecting vital signs of the occupant of the respective seat 101y, 101z (as well as detecting seat status, e.g., occupied/unoccupied, by detecting vital signs of an occupant), as well classifying the occupant, such as man, woman, child, pet, and state, e.g. fatigue, stress, drunkenness, drowsiness, of each detected occupant in the seats 101y, 101z, as well as driver speech state recognition, and a seat belt reminder (SBR) for the occupant (once the seat is determined to be occupied). The vital signs detected include, for example, breathing or respiratory rate (RR), heart rate (HR), and heart rate variability (HRV), as well as driver speech state recognition.

The radar from the sensor units 101a-101i is, for example, Doppler radar and operates in one or more modulations including, for example, continuous waveform (CW), FM/PM/AM/Pulse modulations. Each sensor unit 101a-101i generates and receives signals, which, for example, monitor and detect harmonic signals generated by humans, pets, and other live beings, who are typical vehicle cabin occupants. The data associated with the radar of each sensor unit 101a-101i is typically processed in the sensor units 101a-101i (by one or more processors including a central processing unit (CPU) 408 (FIG. 4A)) with the processed data, for example, transmitted via a link to the cellular tower 102, so as to be transmitted to the home server 110 over the network 50. Alternately, some or all of the data associated with the radar of each sensor unit 101a-101i, may be transmitted to the home server 110, via the link to the cellular tower 102, so as to be processed by processors of the home server 110. For example, the harmonic signals transmitted by the sensor units 101a-101i, monitor the pulsing of the heart, aorta or associated veins and other vessels of the heart. Each harmonic signal (e.g., of the heart/heart beat) generates multiple harmonics, as illustrated in FIG. 2.

Figure 2:
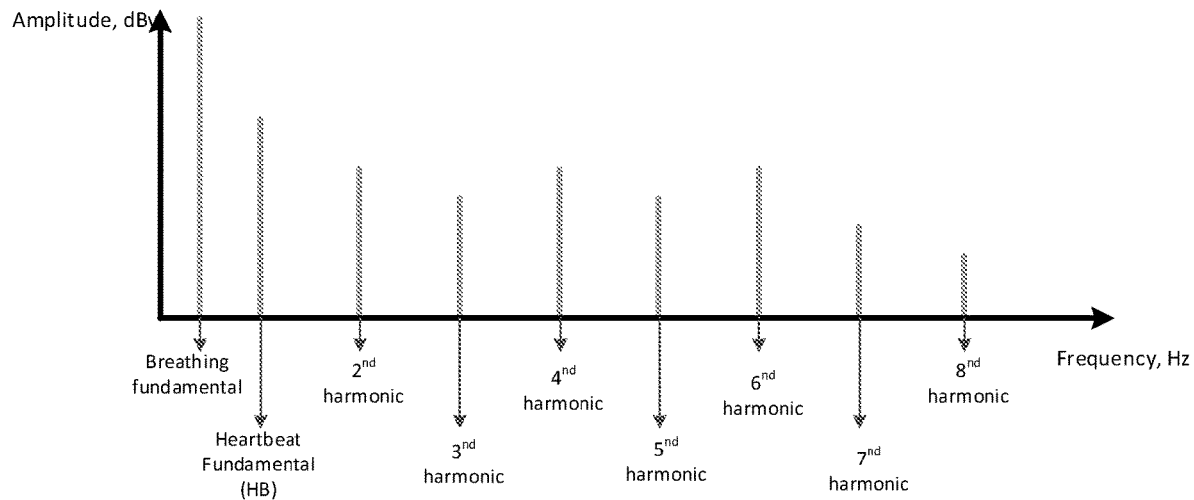
FIG. 2 is graph of the harmonics associated with the breathing rates or heart/heart beat rates.

As shown in FIG. 2, the signal coming from the heart is harmonic, as shown for example, as eight harmonics, first through eighth (vertical lines), of FIG. 2. The radar from each sensor unit 101a-101i, for example, monitors a different section of the body, in order to monitor the heart rate and breathing rate of one or more of the vehicle occupants. The sensor units 101a-101i are able to separate vibrations of the vehicle 100 from the vibrations of the heart, the aorta and associated vessels, by filtering the heart rate based on the heart's frequency of beating (e.g., 0.8 to 3 Hertz (Hz), corresponding to 48 to 180 beats per minute (bpm)).

The sensor units 101a-101i are also programmed to filter the breathing signals (RR) (typically lower frequencies from those of the heart rate (HR) signals), from the heart rate (HR) signals and vehicle vibrations, for analysis. A typical human adult breathing rate is approximately 0.1 Hz to 0.5 Hz, corresponding to 6 to 30 breaths per minute, and for children, approximately, 0.1 Hz to 0.95 Hz, corresponding to up to 55 breaths per minute.

Figure 3A:
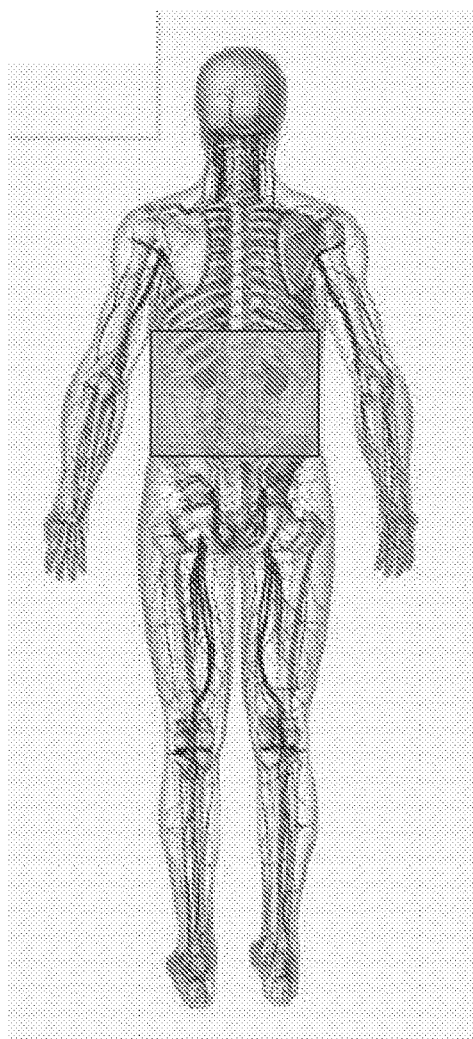
FIG. 3A is a diagram of the human body showing a close distance (near field) location for radar positioning.
Figure 3B:
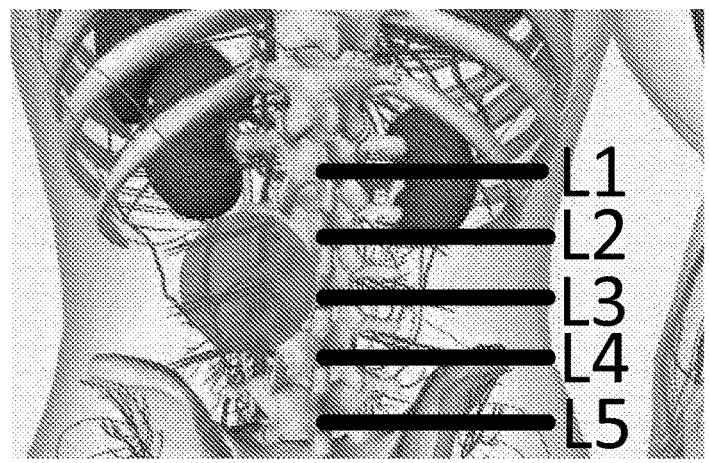
FIG. 3B shows the areas of the lumbar spine for the radar positioning.

For example, the heart rate signals are monitored from the Aorta, which is proximate to vertebrae Lumbar-3 (L3) and Lumbar-4 (L4), as shown in FIG. 3A and FIG. 3B. The aorta is analyzed from the L3, L4 position used, for example, as it undergoes only small movements when a person being monitored is seated in the seats 101y, 101z of the vehicle 100. The breathing rate (respiratory rate) may be monitored from the diaphragm. The sensor units 101a-101i, in particular chair mounts units 101c1-101c3, 101e1-110e3, are located, for example, proximate to the L3, L4 region (for example, so the radar antenna(s) position is located near field for radar beams).

For example, the sensor units 101c1-101c3, 101e1-101e3, mounted or otherwise embedded in the seats 101y, 101z, are typically used in vital signs monitoring.

The algorithms may be performed in the sensor unit 101a-101i, for example, the CPU 408, therein, or the home server 110, or partially in the sensor unit(s) 101a-101i and the home server 110. The algorithms are performed for numerous operations. Example operations include: detecting multiple occupants in the vehicle, by, for example, breath separation, evaluating harmonic features of the detected signals to calculate vital signs, including heart rate (HR) and breathing rate (RR) calculating the heart rate (HR) and Breathing Rate (RR), and from the heart rate, and its corresponding signal, determination of consecutive peaks in the HR signal in the time domain for determining HRV. From the RR and HR signals, the presence or absence of vehicle occupants can be determined, the type of occupant, man, woman, child, animal, as well as the vital signs of human and animal occupants. For example, determining the number of occupants, e.g., human occupants, in a vehicle is useful in the administration of High Occupancy Vehicle (HOV) roadways. Other operations detect occupancy/non-occupancy states of each seat or place for a passenger in the vehicle, and vital signs of each of the detected occupants. The vital sign detection includes, for example, determining heart rate (HR) and breathing rate (BR) of each detected occupant, and heart rate variability (HRV).

FIG. 4A shows sensor unit 101a, representative of the sensor units 101a-101i, as detailed above, presented as an operational unit. Each of the sensor units 101a-101i is positioned in the vehicle as shown in FIG. 1B, and all data is extracted inside each embedded sensor unit 101a-101i. Additional process activity, additional to that of the sensor units 101a-101i, may be performed on the network 50, e.g., by the home server (HS) 110 (as detailed below).

The sensor unit 101a includes a power supply 403, which is, for example, supplied from a vehicle accumulator. The power supply 403 may also be a battery or supplied directly from the vehicle, e.g., the vehicle battery. The power supply 403 may be controlled by the CPU 408. Within the sensor unit 101a, the power supply 403 connects, either directly or indirectly, to all of the system elements, including: an RF radar generator/transmitter/receiver 404, hereinafter "RF transceiver 404" or "RF Radar Transceiver 404", filtering and amplification circuit 406, Analog to Digital convertor (ADC) 407, Central Processing Unit (CPU) 408 (also known as a Signal-processing unit, these terms used interchangeably herein), Digital to Analog (DAC) convertor 405, output/input interface 409 (which communicates with a user interface 410), and an inertial measurement unit (IMU) 411.

The power supply 403, RF transceiver 404, and DAC 405, form an RF modules array. The filtering and amplification circuit 406 forms an IF signal processing unit, with the Analog to Digital convertor (ADC) 407. The CPU 408 includes one or more processors, including hardware processors, such as processors commercially available from Intel, AMD and the like.

The power supply 403 provides power for the RF transceiver 404, DAC 405, filtering and amplification circuit 406, ADC 407, and CPU 408. The sensor unit 101a, is such that elements 403, 404, 405, 406, 407, 408, 409, and 411, are typically in the sensor unit 101a as embedded elements in a single housing H.

The user interface 410, may be either a wired or wireless interface. The interface 410 may also be integrated as part of the vehicle, as well as a smartphone, tablet, computer or any other embedded interface. This user interface 410, or alternately, the output/input interface 409 links to the network(s) 50, so as to be in electronic and data communication with the home server 110, which runs the various algorithms, and sends the data outputted by these algorithms to the various entities, represented by servers 121, 122 and 123.

The RF radar transceiver 404 is, for example, Doppler radar and operates in one or more modulations including, for example, continuous waveform (CW), FM/PM/AM/Pulse modulations. The RF Radar Transceiver 404 includes one or more antennas (including radar antennas), which transmit RF high frequency signals and receive the reflected signals from the object (e.g., vehicle occupant(s)), and converters for converting the reflected (an received) high frequency RF signals to Intermediate frequency (IF) signals.

This RF radar (from the RF transceiver 404) is such that if the output is a single output, for example, an analog signal, or a dual output of two signals, also analog signals, the first is "Q" refers to quadrature data and second "I" refers to in-phase data.

The RF radar transceiver 404 operates, for example, in one or several frequency bands. Preferably, the RF radar operates in X (8 to 12 GHz), Ku (12 to 18 GHz), K (18 to 27 GHz), K(ISM) (24.05 GHz to 24.25 GHZ) and W (75 to 110 GHz).

The filtering and amplification circuit 406 performs operations, including, for example, filtering IF (intermediate frequency) signals transmitted from the RF radar 404. In this circuit 406, unwanted frequencies are filtered out, letting the desired frequencies pass through to the ADC 407. The filtering and amplification circuit 406 includes, for example, filters and amplifiers.

The filters, for example, are for various frequencies, and may be hardware, software or combinations thereof. The filters clean the IF signals of noise and prevent aliasing before data acquisition.

The amplifiers amplify the IF signals before the IF signals enter the ADC 407. The amplifiers, for example, are for various frequencies, and may be hardware, software or combinations thereof.

The filtering and amplification circuit 406 operates in two variations of output from the RF radar 404, for example, as: 1) a single analog output, formed of a filtering and amplification circuit for amplifying a single analog data transfer from the RF radar 404; and 2) "I" (in phase) and "Q" (quadrature) outputs from RF radar 404, two filtering and amplification circuits for amplifying the RF radar 404 "I" and "Q" outputs.

The ADC 407, converts the signal-received from the filtering and amplification circuit 406 from an analog to a digital signal. The ADC 407 may be a separate module or embedded into the CPU 408. When the ADC 407 is separate from the CPU 408, it transmits digital signal (raw data) to the CPU 408. The ADC 407 converts the filtered analog signals received from the filtering and amplification circuit 406, to digital signals data to allow digital processing by the processing algorithms of CPU 408, including those to determine breathing rate (RR), heart rate (HR) and heart rate variability (HRV). The CPU 408 receives raw data from the ADC 407 when the ADC 407 is separate from the CPU 408. Alternately, the CPU 408, for example, receives an analog data state from the filtering and amplification circuit 406. In this case, the CPU 408 converts the analog signal to a digital signal (raw data). The aforementioned analog signal(s), (e.g., IF signals) from the filtering and amplification circuit 406, and the corresponding signals reproduced by the CPU 408 from the digital signal provided by the ADC 407, include one or more peaks.

The CPU 408 processes the data via vital signs detection algorithms, based on analyzing various signals generated by the vehicle occupants, i.e., humans, pets, and the like, and calculates the heart rate, respiratory rate and/or movement of the person or pet.

The CPU 408 forwards monitored data to the output interface 409.

The CPU 408 is, for example, based on any embedded or real time processor that is suitable for operating a vital signs monitoring algorithm. The CPU 408 is agnostic to computer operating systems (OS).

The algorithms may be performed in the CPU 408, the home server 110, or partially in the CPU 408 and the home server 110. The algorithms can also be run on any electronic control unit (ECU) of the vehicle, which includes for example, the CPU 408. The algorithms are performed for numerous operations. Example operations include: detecting multiple occupants in the vehicle, by, for example, breath separation, evaluating harmonic features of the detected signals to calculate vital signs, including heart rate (HR) and breathing rate (RR) calculating the heart rate (HR) and Breathing Rate (RR), and from the heart rate, and its corresponding signal, determination of consecutive peaks in the HR signal in the time domain for determining HRV. From the RR and HR signals, the presence or absence of vehicle occupants can be determined, the type of occupant, man, woman, child, animal, as well as the vital signs of human and animal occupants. For example, determining the number of occupants, e.g., human occupants, in a vehicle is useful in the administration of High Occupancy Vehicle (HOV) roadways. Other operations detect occupancy/non-occupancy states of each seat or place for a passenger in the vehicle, and vital signs of each of the detected occupants. The vital sign detection includes, for example, determining heart rate (HR) and breathing rate (BR) of each detected occupant, and heart rate variability (HRV). Output/input interface 409 is, for example, a wired or wireless interface. The interface 409 functions, for example, to forward vital signs monitor data to a user interface 410, as well as raw data, such as the data from the filtering and amplification circuit 406, ADC 407 and the IMU 411, such that the data can be processed, e.g., to detect vial signs of occupants, in the home server 110 and ECU (e.g., external ECU). The output/input interface is also capable to receive information such internal configurations, triggering, user data and the like.

Optionally, the sensor unit 101a can use the digital to analog convertor (DAC) 405 for modulation of frequency changes by applying the analog signal from the DAC 405 to the TRX element of the radar transceiver 404 VCO (voltage control oscillator) of the RF radar transceiver 404. The DAC 405 while shown as a separate system component, may also be integrated into the CPU 408. When the CPU 408 includes a DAC 405 and/or an ADC 407, the DAC 405 and/or ADC 407 is bypassed or/and removed from the system of the sensor unit 101a-101i.

The IMU 411 includes a magnetometer, gyrometer and accelerometer, to detect various movements and vibrations of the vehicle. The IMU 411 links to the CPU 408 to provide data concerning the movements and vibrations of the vehicle. The CPU 408 factors this movement data into its analysis to determine RR, HR and HRV, as detailed further below.

Figure 4B:
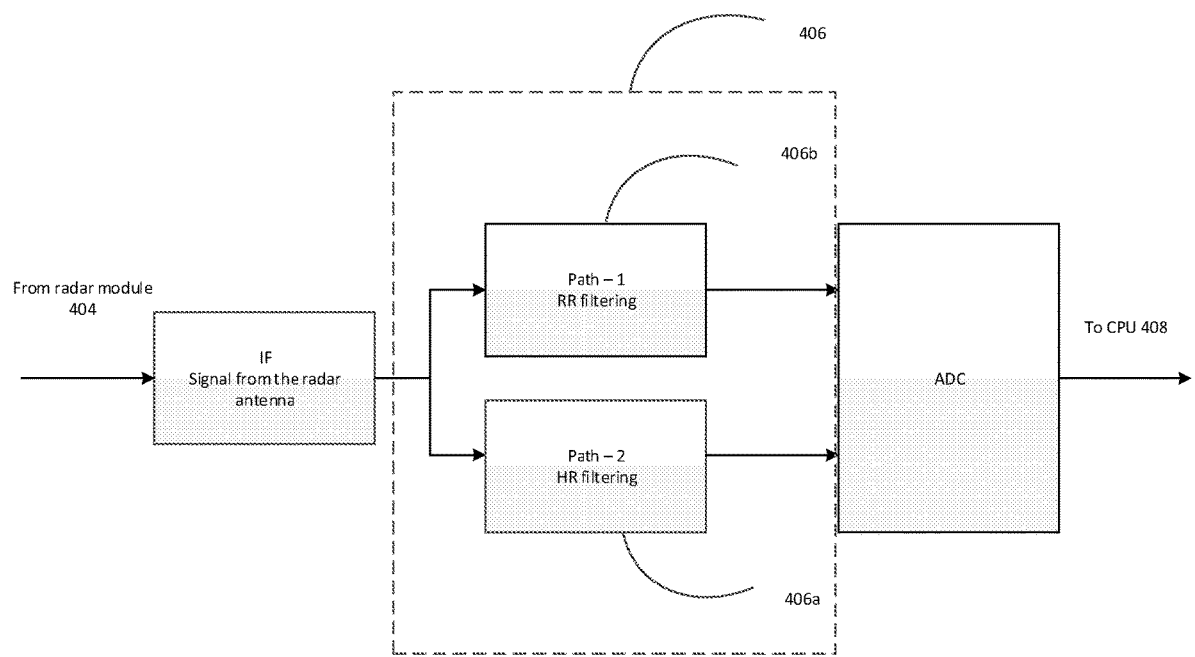
FIG. 4B is a diagram of a portion of the sensor unit of FIG. 4A.

FIG. 4B is a schematic diagram showing the filtering and amplification circuit 406, configured for two pathways. By having the two pathways for breathing rate 406a (a higher amplitude signal than the heart rate), and heart rate 406b, higher signal to noise ratio (SNR) of the obtained signal (by the ADC 407) is achieved. A first pathway 406a for breathing rate filtering, and a second pathway 406b for heart rate/heart rate variability filtering. For example, on the first pathway 406a, filtration is from approximately 0.3 to 3 Hz for initial conditions and start up, while on the second pathway 406b filtration is from approximately 0.8 to 20 Hz for initial conditions or start up.

Figure 4C:
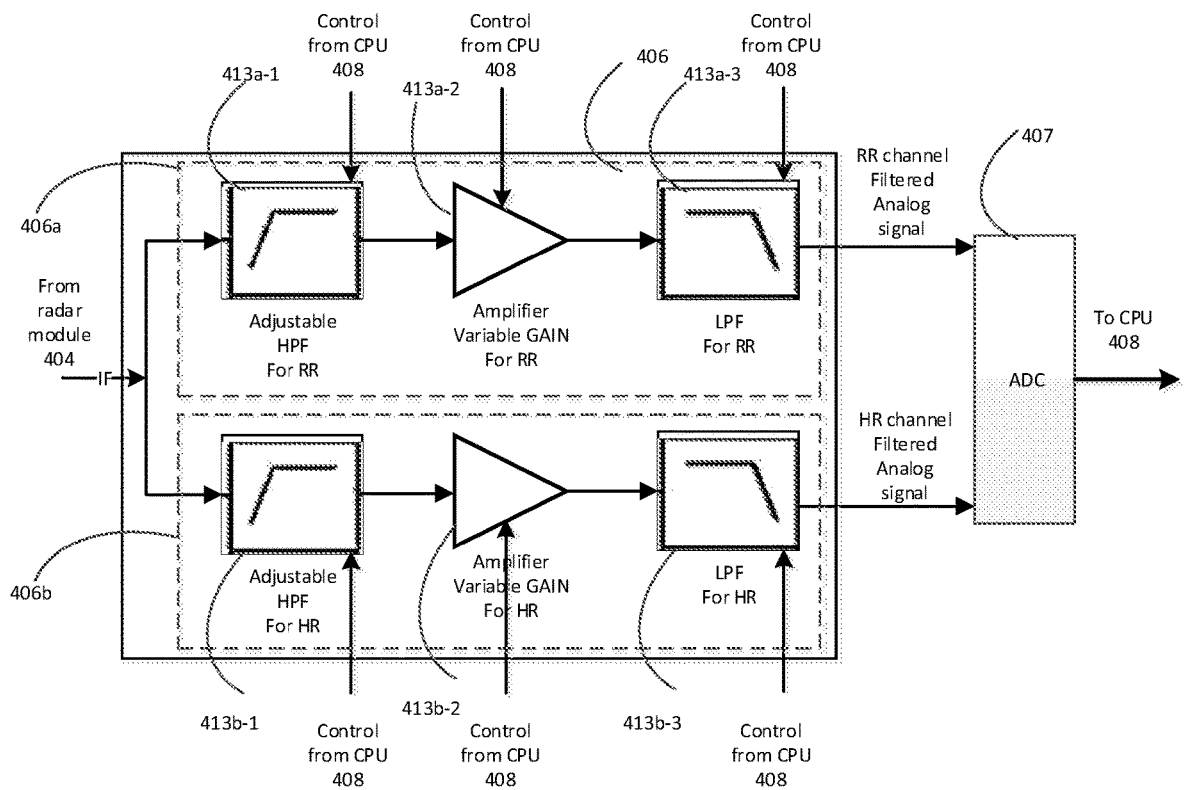
FIG. 4C is a diagram of the filtering and amplification circuit of FIG. 4A.

FIG. 4C is a diagram of the components of the filtration and amplification circuit 406 for the breathing rate 406a and heartrate/heart rate variability 406b pathways. Both pathways 406a. 406b receive IF signal input from the RF Radar transceiver 404, and output a filtered analog signal within the frequency band set along each pathway 406a, 406b, to the analog to digital converted ADC 407. The frequency bands are as narrow as possible, so as to have all noise in the band eliminated, so as to have a readable signal. Each pathway 406a, 406b includes a high pass filter (HPF) 413a-1, 413b-1, an amplifier 413a-2, 413b-2, and a low pass filter 413a-3, 413b-3 (LPF). The high pass filters 413a-1, 413b-1, amplifiers 413a-2, 413b-2, and low pass filters 413a-3, 413b-3, are, for example, controlled by the CPU 408, as detailed below.

Along both pathways, the high pass filter (HPF) 413a-1, 413b-1 sets an edge for the signal, which is at a frequency, lower than the breathing rate (RR), in the breathing rate pathway 406a, and a frequency, lower than the heart rate (HR), in the heart rate pathway 406b. The amplifiers 413a-2, 413b-2 apply gain, in accordance with the calibration method detailed below, so as to amply the signal to an amplitude suitable to separate noise from the signal. The low pass filters 413a-3, 413b-3, set an upper edge for the signal, which is at a frequency, higher than the breathing rate (RR), in the breathing rate pathway 406a, and a frequency, higher than the heart rate (HR), in the heart rate pathway 406b.

Calibration Method

A calibration method is performed in order to determine the minimal gain level for the analog amplifiers 413a-2, 413b-2, and the optimal filtering ranges. The calibration method is typically performed when the vehicle cabin 101x is empty.

The following steps are performed for a calibration. The radar transceiver 404 voltage control oscillator (VCO) level, is changed, from the DAC 407 or the CPU 408. The change is based on VCO levels referenced to the heart rate frequencies. This is done by modulating the RF signal (transmitted form the radar transceiver 404) at the frequency of heart rate (may be used few frequencies: lower HR, mid HR, high HR), in order to cover the entire frequency band.

If the radar transceiver 404 does not have a VCO, it is possible to change the voltage supply of the radar transceiver 404, in order to change the transmitted (RF) frequency. This is done by changing the power supply 403, in order to change the voltage level. This change in voltage level will impact on the transmitted RF frequency form the radar transceiver 404.

For methods described above, the modulated signal from the radar transceiver 404 is typically done when the vehicle cabin 101x is empty. The reflected signal received from the radar transceiver 404, at the minimal power level, which may be received by the radar transceiver 404. The calibration of the gain levels of the radar RF (LNA) and IF signals should be based on the specific lower signal level which was received while the vehicle 100 was empty. For example, the gain level should allow for receipt of reflected calibration signals (waveforms) at the SNR ratio of at least 1 dB (decibel). In the case of calibration over multiple frequencies, for example, low, mid, high, the mean gain should be selected by the CPU 408 (by the preprogrammed initial settings).

Figure 5A:
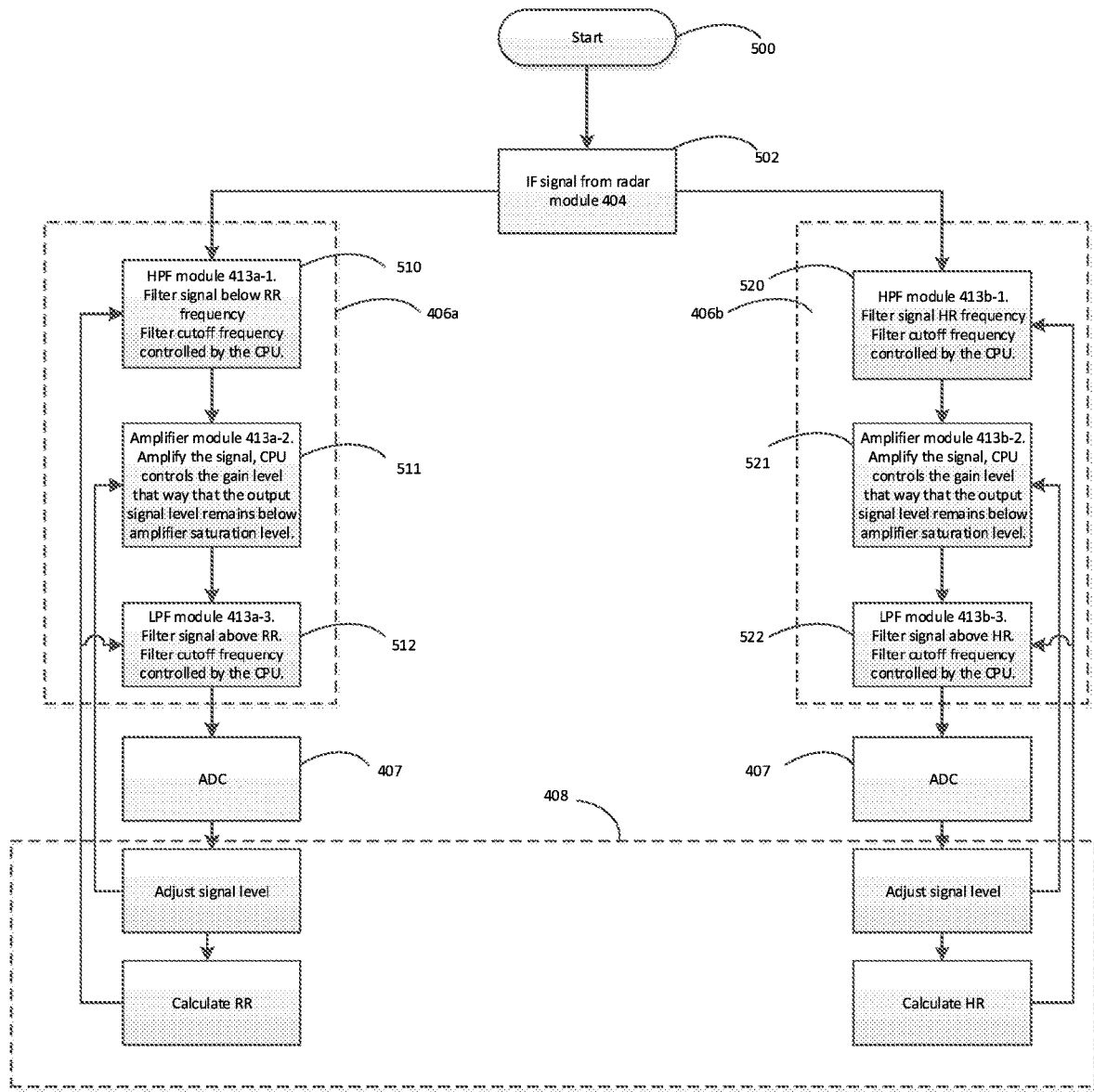
FIG. 5A is a flow diagram of a process for processing a signal by the sensor unit.

FIG. 5A is a flow diagram for processes performed by the filtration and amplification circuit 406 of FIGS. 4A-4C, to isolate a signal usable for the breathing rate (RR), and heart rate (HR).

The process begins at block 500. At this start block 500, the filters and amplifiers are set to initial conditions, for example, 0.3 Hz to 3 Hz for filters along the breathing rate pathway 406a, and 0.8 to 20 Hz for the filters along the heart rate pathway 406b, with amplifier gain initially set by the calibration method (default condition is no gain), detailed above. At block 502, an IF signal, received from the RF Radar transceiver 404 (received as a result of the radar) is sent, and processed along the breathing rate pathway 406a and heart rate pathway 406b.

Moving along the breathing rate pathway 406a, the process moves to block 510. At block 510, the adjustable high pass filter (HPF) 413a-1 is adjusted to filter out unwanted signals below predetermined levels. For example, the passband (e.g., predetermined level) is initially, or otherwise starts from, and at least approximately 0.1 Hz. At block 511, the analog amplifier 413a-2 is referenced to the input signal, as measured by the CPU 408. This adjustment is made such that the output signal from the amplifier 413a-2, remains in the linear region. The process moves to block 512, where the adjustable low pass filter (LPF) 413a-3, is adjusted for the breathing rate, to filter out unwanted high frequency signals. The cut off frequency is set by the CPU 408 (FIG. 5B), with cut off values preprogrammed into the system of the CPU 408, or the CPU 408 is provided with a look up table (LUT).

The CPU 408 also analyzes the signal to noise ratio, and whether the breathing rate signal is harmonic. The breathing rate signal is considered to be harmonic when the person is breathing (not speaking) periodically. For analyzing the breathing rate, at least eight harmonics should be evaluated, so as to form the breathing rate signal. For example, for a measured breathing rate frequency of 0.3 Hz, and the signal is harmonic, the cut off frequency of the low pass filter 413a-3 is determined by a multiplier, e.g., "10" (so as to, for example, evaluate at least eight harmonics, two extra harmonics resulting in 10 harmonics) multiplied by the breathing rate frequency, e.g., 0.3 Hz, for a 3 Hz cut off. From block 512, the output signal is sent to the ADC 407.

Returning to block 502 and moving along the heart rate pathway 406b, the process moves to block 520. At block 520, the adjustable high pass filter 413b-1 is adjusted to filter out unwanted signals below predetermined levels. For example, the passband (e.g., predetermined level) is at least approximately 0.8 Hz. At block 521, the analog amplifier 413b-2 is referenced to the input signal, as measured by the CPU 408. This adjustment is made such that the output signal from the amplifier 413b-2, remains in the linear region. The process moves to block 522, where the adjustable low pass filter 413b-3, is adjusted for the HR/HRV, to filter out unwanted high frequency signals. The cut off frequency is set by the CPU 408, with cut off values preprogrammed into the system of the CPU 408 is provided with a look up table (LUT).

The CPU 408 also analyzes the signal to noise ratio and the harmonics weight coefficient algorithm, detailed below. Evaluation of the HR is based on the number of harmonics to be measured. For example, for a measured HR frequency of 1.5 Hz, and the cut off frequency may be a multiplier of 16 (the heart beat is in four motions QRST, for each of the two atria and the two ventricles—4 motions by 4 chambers is 16, the multiplier). The HR frequency, e.g., 1.5 Hz, is multiplied the multiplier of 16, for a 24 Hz cut off. From block 522, the output signal is sent to the ADC 407.

Figure 5B:
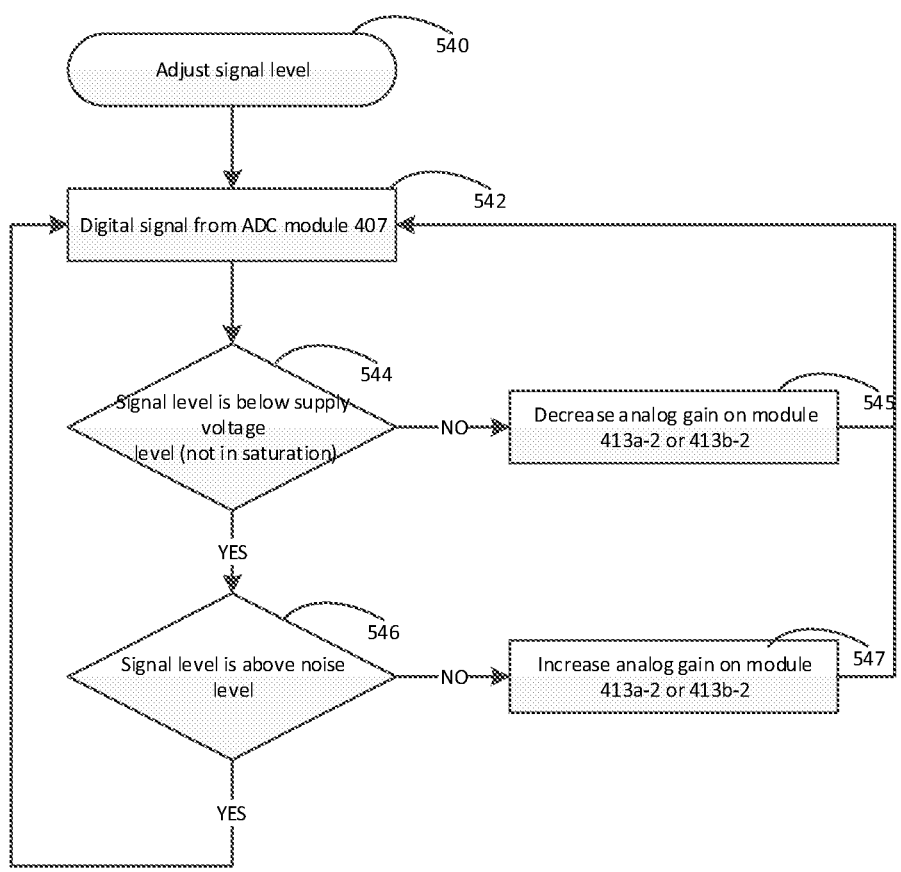
FIG. 5B is a flow diagram for amplifier operation for the sensor unit defined in FIG. 5A.

For both pathways 406a, 406b the ADC sends the signal to the CPU 408, which adjusts the signal level, with a closed loop to the respective amplifier 413a-2, 413b-2, and adjusts the filter high pass and low pass frequency cut-offs, in accordance with the process of FIG. 5B. For the heart rate path 406b, the high pass filter frequency cut off of block 520, is set above the heart rate frequency, after determining the heart rate. This is done movements of a seated occupancy, which the vehicle is in the range of the heart rate frequency. In this case, only the heart rate harmonics are analyzed by the CPU 408, and the heart rate (HR) and heart rate variability (HRV) are extracted from this analysis.

FIG. 5B is a diagram of process performed by the CPU 408 for the signal level of the frequency band, for example, by adjusting gain in the amplifiers 413a-2, 413b-2. Initially, the process starts at block 540, where gain is initially set by the calibration method above. The process moves to block 542, where the signal sent to the ADC 407 is recorded. The process moves to block 544, where it is determined whether the signal level is below the supply voltage of the amplifier 413a-2, 413b-2. If no, the process moves to block 545, where analog gain on the signal is decreased by the respective amplifier 413*a*-2, 413*b*-2. The process then moves to block 542, from where it resumes.

If yes at block 544, the process moves to block 546. At block 546, it is determined whether the signal level is above the noise level. If no, the process moves to block 547, where analog gain on the signal is increased by the respective amplifier 413*a*-2, 413*b*-2. The process then moves to block 542, where it continues.

If yes at block 546, there is no gain adjustment by the respective amplifier 413*a*-2, 413*b*-2. The process returns to block 542, from where it resumes.

Figure 6:
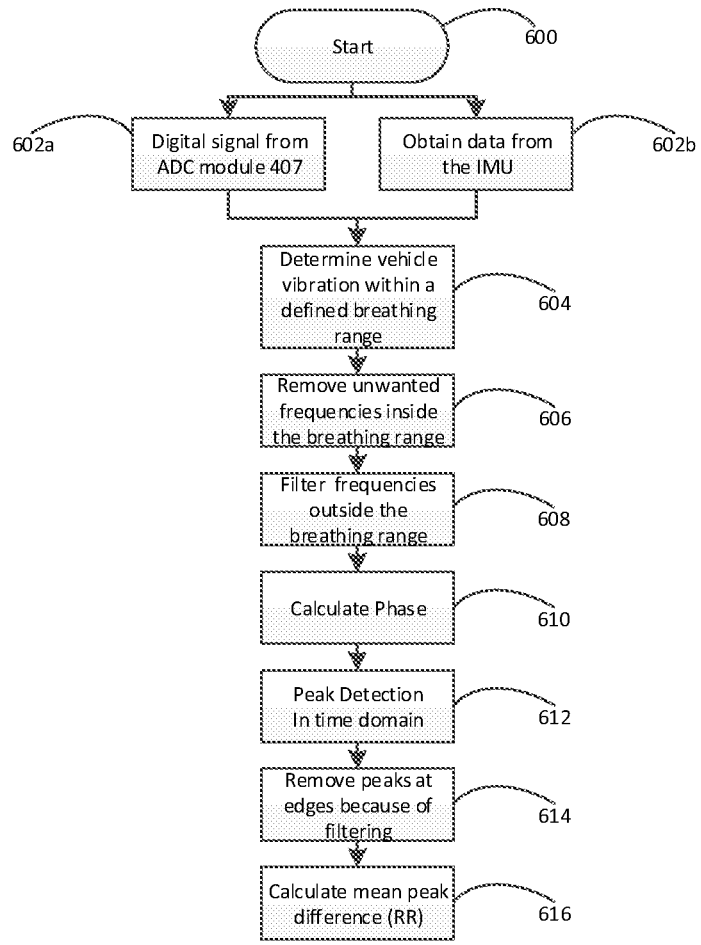
FIG. 6 is a flow diagram for a process for determining the breathing or respiratory rate of a vehicle occupant in accordance with embodiments of the invention.

FIG. 6 is a flow diagram detailing an exemplary process for determining the breathing or respiratory rate (RR) of a vehicle occupant, for example, by a sensor unit, such as sensor unit 101*a*, representative of all sensor units 101*a*-101*i*. The process starts at block 600, and moves to blocks 602*a* and 602*b*, where contemporaneous, e.g., simultaneous, processes are performed.

At block 602*a*, a digital signal, converted from the analog signal, which was captured by the radar transceiver 404 for the occupant, is received in the CPU 408. The digital signal is reformed by the CPU 408 and typically includes I and Q portions. At block 602*b*, data as to vibrations associated with the vehicle is obtained from the IMU 411, by the CPU 408. From blocks 602*a* and 602*b*, the process moves to block 604, where the vehicle vibration data is determined within a defined breathing range. This predetermined (defined) breathing range, for example, is determined by the high pass 413*a*-1 and low pass 413*a*-3 filters and from an initial start of 0.1 to 0.5 Hz. The process moves to block 606, where unwanted frequencies, the frequencies which are measured by the IMU 411 within the breathing range frequency band, inside the breathing range are removed, for example, by digital filtration.

The process moves to block 608, where frequencies outside the breathing range for example, is determined by the high pass 413*a*-1 and low pass 413*a*-3 filters and from an initial start (of 0.1 to 0.5 Hz) are digitally filtered. At block 610, the phase for the digital signal is calculated. This phase Φ is calculated as:

$$\Phi=\arctan(Q/I)$$

The process moves to block 612, where the peaks of the filtered signal are detected in the time domain. At block 614, the peaks at the edges of the time window in which the signal is analyzed, are removed, as they may have been affected (changed) by the filtration itself. From the existing peaks, within the time window, the mean peak to peak distance is calculated, at block 616. This mean peak to peak distance is the breathing or respiratory rate (RR).

Figure 7A:
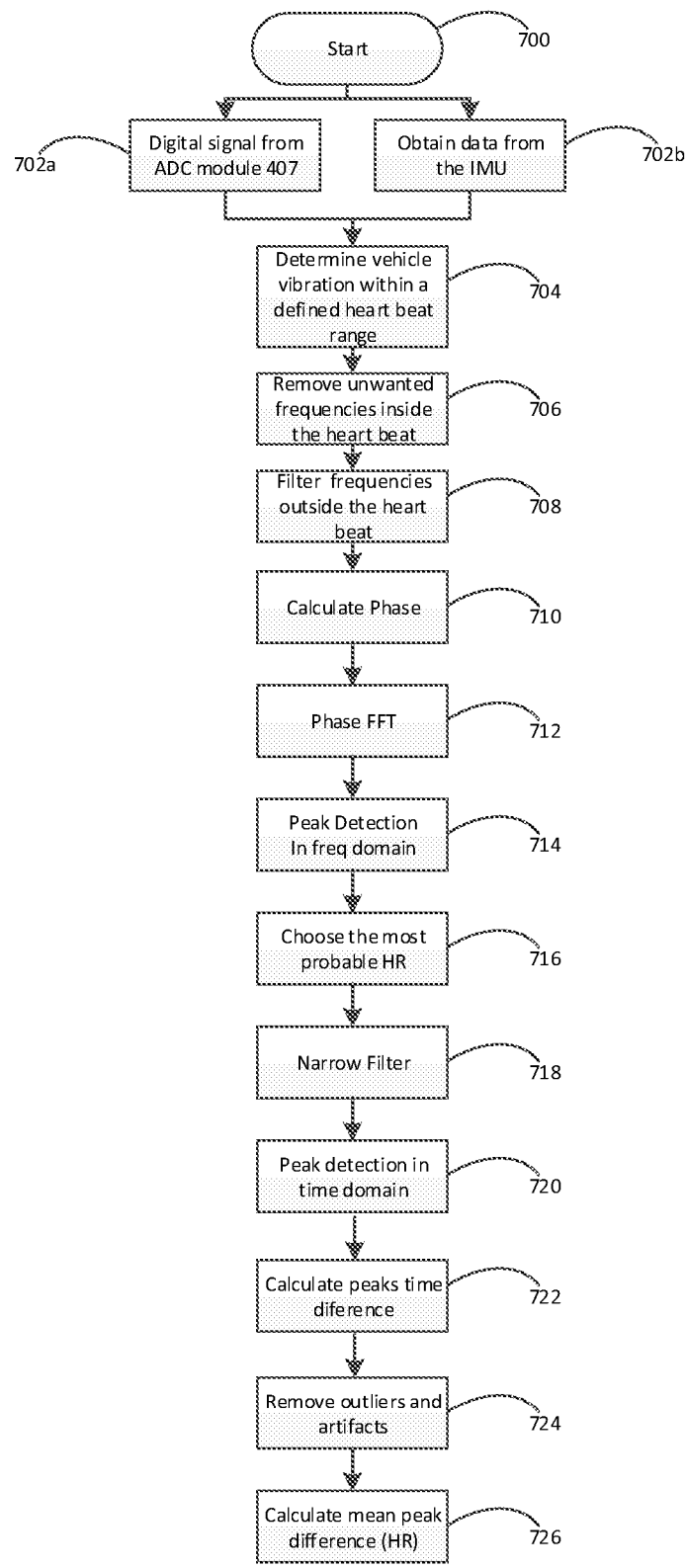
FIG. 7A is a flow diagram for a process for determining the heart rate of a vehicle occupant in accordance with embodiments of the invention.

FIG. 7A is a flow diagram detailing an exemplary process for determining the heart rate (HR) of a vehicle occupant, for example, by a sensor unit, such as sensor unit 101*a*, representative of all sensor units 101*a*-101*i*. The process starts at block 700, and moves to blocks 702*a* and 702*b*, where contemporaneous, e.g., simultaneous, processes are performed.

At block 702*a*, a digital signal, converted from the analog signal, which was captured by the radar transceiver 404 for the occupant, is received in the CPU 408. The digital signal is reformed by the CPU 408 and typically includes I and Q portions. At block 702*b*, data as to vibrations associated with the vehicle is obtained from the IMU 411, by the CPU 408. From blocks 702*a* and 702*b*, the process moves to block 704, where the vehicle vibration data is determined within a defined heart rate range. This predetermined heart rate range, for example, is determined by the high pass 413*b*-1 and low pass 413*b*-3 filters and from an initial start of 0.8 to 3 Hz. The process moves to block 706, where unwanted frequencies, the frequencies which are measured by the IMU 411 within the heart rate frequency band, inside the heart rate range are removed, for example, by digital filtration.

The process moves to block 708, where frequencies outside the breathing range (the breathing range, for example, is determined by the high pass 413*b*-1 and low pass 413*b*-3 filters and from an initial start of 0.8 to 3 Hz) are digitally filtered. At block 710, the phase for the digital signal is calculated. This phase Φ is calculated as:

$$\Phi=\arctan(Q/I)$$

The process moves to block 712, where a phase Fast Fourier Transform (FFT) is performed on the signal, to transform the signal from the time domain to the frequency domain. The process moves to block 714, where peak detection for the signal is performed in the frequency domain.

Figure 7B:
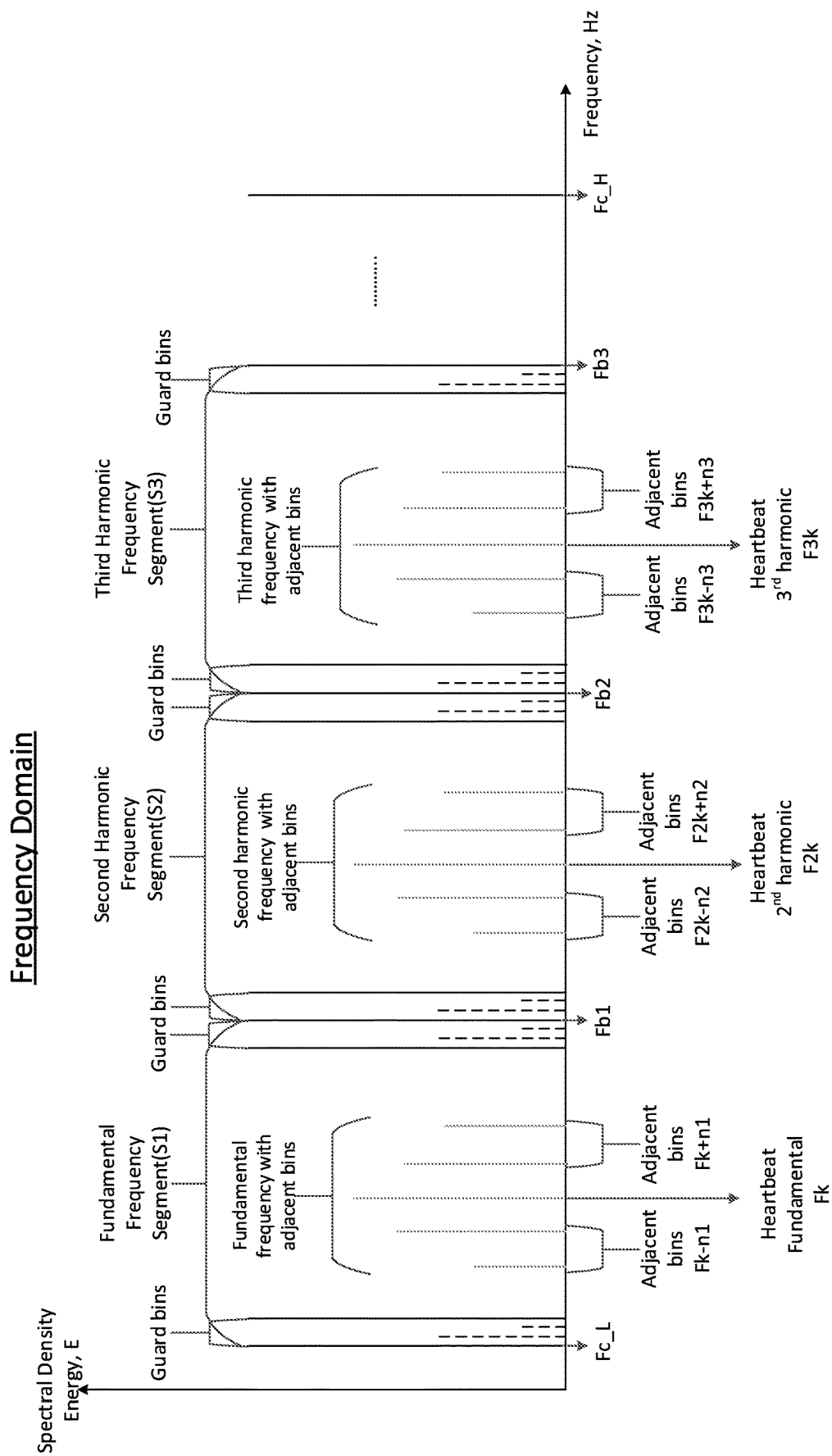
FIG. 7B is a diagram of frequencies used with the flow diagram of FIG. 7A.

The process now moves to block 716, where the most probable heart rate (HR) is determined. This most probable heart rate (HR) is determined with reference to FIG. 7B, for example, as follows:

1. Define Parameters for FIG. 7B:
    a. $F_k$ is the central bin frequency of the signal (Complex FFT could be taken for example, if I and Q signals are obtained)
    b. $E_k$ is the energy value into the bin of k
    c. k is an integer number of a bin
    d. i represents the harmonic number (see FIG. 2)
    e. $F_{bi}$ is the fundamental frequency segment Si border frequency
    f. $F_{c\_L}$ is the cut off frequency of the Adjustable high pass filter 413*b*-1 and determines the start frequency border of the first segment (S1)
    g. $F_{c\_H}$ is the cut off frequency of the Adjustable low pass filter 413*b*-3
2. The signal is filtered by the adjustable high pass filter 413*b*-1, with a cut off frequency $F_{c\_L}$ determined after calibration with default value of 0.8 Hz, for example.
3. The signal is filtered using the adjustable low pass filter 413*b*-3 with a cut off frequency $F_{c\_H}$ determined after calibration with a default value of 20 Hz, for example.
4. Accumulation procedures are performed for each frequency within the $F_k$ frequency:
    a. Share frequency band between $F_{c\_L}$ and $F_{c\_H}$ on frequency segments (sub-bands) corresponding to the fundamental frequency $F_k$ and its harmonics ($F_{2k}$, $F_{3k}$ . . . ). The Border Frequency ($F_{bi}$ to $F_b(i+1)$) between the segments i and i+1 may be calculated using a defined function, for example as geometric average $F_{bi}=F_k \times \sqrt{i \times (i+1)}$ or predefined in a Look Up Table (LUT).
    b. Calculate the energies of bins around $F_{i \times k}$ frequencies which including $E_{i \times k}$ energy and adjacent bins energies around these frequencies. Calculation is by the following function:
    $Ea_{i \times k}=\Sigma_{m=i \times k-Bins(i \times k)}^{i \times k+Bins(i \times k)} E_m$, for example in FIG. 7B, Bins(i×k)=$n_i$; i=1,2,3 where n is an integer number.
    c. The number of adjacent bins may be defined by a function or by a BIN LUT. This number is related to expected deviation because of the Heart Rate signal (analog signal received from the filtering and amplification circuit 406). For example a simple function can be: Bins(k)=1 d. Calculate the total energy of the bins for each segment $E_{si}$ (obtain the sum of all bins of a segment S)
e. Multiply the energy calculated in Part b above by a Weight coefficient $W_{i \times k}(R)$, argument of which (R) is the ratio between the energy $Ea_{i \times k}$ calculated in Part b and the and the segment S energy: $R=Ea_{i \times k}/Es_i$ the function may be calculated by a defined function (for Example $W_{i \times k}(R)=R^2$) or it may be defined from a corresponding LUT.
f. Accumulate multiplications of k frequency by up to the number of the harmonics that are taken into account (one or more up to the $F_{c\_H}$), and apply the formula AF, for $F_k$ frequency as follows:

$$AF_k = \sum_{i=1}^{num\_harmonics} Ea_{i \times k} \times W_{i \times k}$$

for example, for three harmonics and 1 bin around central bin frequency we accumulate $(E_{k-1}+E_k+E_{k+1}) \times W_k + (E_{2k-1}+E_{2k}+E_{2k+1}) \times W_{2k}+(E_{3k-1}+E_{3k}+E_{3k+1}) \times W_{3k}$
g. Guard bins function can be used to determine the gap interval between the frequency segments, the energy bins which isn't taken into account, default value of 0 (no guard bins).
5. Accumulation is done for each $F_k$ frequency range between $F_{k\_min}$ to $F_{k\_max}$ which default values can be from 0.8 Hz to 3 Hz corresponding to 48-180 HR.
6. The most probable HR correspond the $F_k$ frequency for which a value of the accumulation function $AF_k$ (part 4f) is maximal.

The resultant signal from block 716 is subjected to additional digital filtering at block 718. This additional digital filtering is performed to eliminate unwanted frequencies above and below a predetermined amount from both ends of the HR frequency. For example, if the HR frequency is 2 Hz, the lower end frequency would be lower than 1.6 Hz, and the upper end frequency would be higher than 2.4 Hz, so that the unwanted frequencies eliminated are outside±20%. (the predetermined amount).

Next, the process moves to block 720, where peak detection in the time domain is performed for the signal. This peak detection is a mathematical process for finding local maxima.

The process moves to block 722, where the time difference between each of the peaks, including multiple variations thereof (e.g., peak 1 to peak 2, peak 1 to peak 3, peak 2 to peak 3), in the time domain is calculated.

The process moves to block 724, where outlying peaks and artifacts are also removed from the signal. Artifacts include, for example, unreasonable peak differences (e.g., peak distances much shorter or much larger than that for the calculated heart rate), abnormal peak distances when compared to previous peak distances, and the like. The process then concludes at block 726, where the mean peak to peak differences are calculated, from the peaks that remain. At block 726, the heart rate (HR) is calculated as follows:

HR=[1/mean_peak to peak_difference (in seconds)]·60

Figure 8:
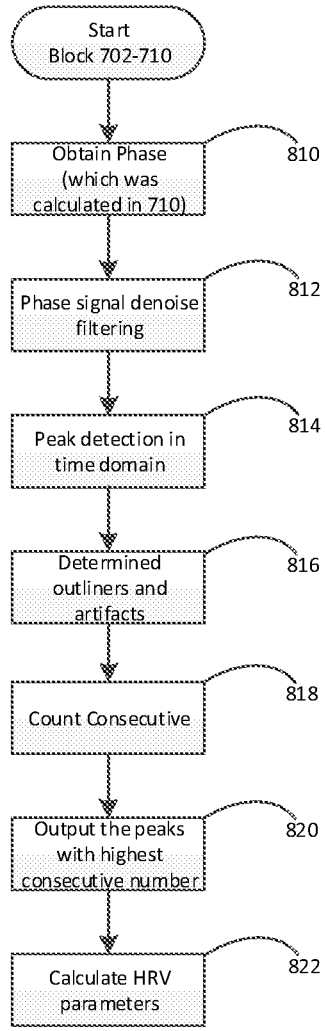
FIG. 8 is a flow diagram for a process for determining the heart rate variability of a vehicle occupant in accordance with embodiments of the invention.

FIG. 8 is a flow diagram detailing an exemplary process for determining the heart rate variability (HRV) of a vehicle occupant, for example, by a sensor unit, such as sensor unit 101a, representative of all sensor units 101a-101i. The process employs the processes of 702a, 702b, 704, 706, 708 and 710 for determining heart rate, and continues from block 810, where the phase for the digital signal is obtained from block 710.

The process moves to block 812, where a phase signal denoise filtering occurs. This occurs, for example, by wavelets and or wavelet decomposition. The process moves to block 814, where peak detection for the signal in this time window is performed in the time domain.

The process moves to block 816, where outlying peaks and artifacts are also removed from the signal. Artifacts include, for example, unreasonable peak differences (e.g., peak distances much shorter or much larger than that for the calculated heart rate), abnormal peak distances when compared to previous peak distances.

The process moves to block 818, where consecutive peaks are counted based on the artifacts, which were determined in block 816. The process moves to block 820, where a series of consecutive peaks, of at least a predetermined number, e.g., 15, is determined.

The process moves to block 822, to calculate the HRV parameters, based on the peak to peak difference between consecutive peaks (the consecutive peaks received from block 820). For example, the HRV parameters include the root mean square successive differences (RMSSD) and/or standard deviation normal (end) to normal (end) (SDNN) of the consecutive peaks.

Objects can also be detected in vehicle cabins, based on the processes detailed above in FIGS. 6, 7 and 8. These objects include, for example, adults, children, infants and pets, who may be left in a vehicle cabin, while the vehicle (e.g., automobile, bus, or school bus) is idling or turned off (not in motion). The method includes combining the IMU 411 data in order to remove the environmental impact on the analyzed signal, which can cause false detection. The method includes, detecting vital signs of potential occupants who have remained in the vehicle. The detection process includes: transmitting a radar signal to vehicle cabin and receiving the reflected signal; analyzing the reflected signal with respect to vibration data of the vehicle to produce a modified signal: and, analyzing the modified signal to determine the presence of vital signs in the vehicle cabin. Should vital signs be present, an occupant has been detected in the vehicle cabin.

This method can be easily adapted to airplanes, ships and the like, for use with caged (or uncages) pets and other animals in cargo holds. This method can also be used for enclosed spaces.

With the data having been obtained as to vehicle the system, for example at the home server 110 can perform various applications of the data. For example, once it is determined that the vehicle cabin 101x includes occupants, a seat belt reminder can be transmitted to the vehicle for the passengers. Passengers can be counted for tolls, cab fares, record keeping, for example for transport companies. Transport companies 122, by knowing the numbers of passengers traveling on a certain route at a certain time can allocate their vehicle fleets accordingly. The number of passengers in a vehicle can be transmitted to first responders 121, such as emergency vehicles and ambulances so a dispatcher can know how many ambulances to send to an accident scene.

Additionally, the number of occupants can be used to monitor traffic and traffic jams, by finding out how many people are traveling on a certain route at any given time. This way, police 121 and municipal authorities 122, as well as statistics companies 123 can know: the amount of people affected by the traffic jam; and, the size of the traffic jam. The amount of people involved in a traffic jam is provided by the system of the invention. The amount of people affected by the traffic jam can be provided by mobile/vehicle applications.

While the invention is shown in use with an automobile, it is usable in multiple vehicles, such as busses, commercial vehicles, trains, boats, airplanes, space vehicles, and the like.

The invention also monitors vital signs, such as heart rate (HR), respiration rate or breathing rate (BR), and heart rate variability (HRV). The monitored vital signs of each individual occupant can be collected and stored for further use. The vital signs recorded can be used to identify a person, via a unique personal pattern as a combination of vital signs data. By one time supplying the passenger names, the system can correlate the person with his/her unique personal pattern.

Additionally, once a person is recognized via his vital signs, the vehicle can recognize the person and settings in the vehicle, can be adapted automatically for the passenger. Some settings include, for example: seat position, seatbelt configuration, seat back position, steering wheel height, and the like. Once the occupants are detected by the system, as men, women, children, and the like. Knowing this information, as sent by the system, content, e.g., music, video, and the like, from a content provider, can be sent to the vehicle, based on its occupants.

The vital sign identification provided by the system can also be indicative of a persons state, such as fatigue, drug or alcohol inebriation, and the like.

The system also recognizes vital signs of animals in the vehicle, including those being shipped as cargo.

The system can also collect personal vital signs for each passenger over the course of a journey, so as to detect sicknesses, medical conditions, and the like.

While the invention has been shown in use inside a vehicle, the invention can also be used outside of the vehicle, in other vehicles such as wheelchairs and other chairs, beds and furniture. The vehicles which the invention may be used, also include, trucks, busses, airplanes (e.g., cockpits and passenger and crew cabins), boats, ships, space vehicles, military vehicles, helicopters, and the like.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse are optionally provided as well.

For example, any combination of one or more non-transitory computer readable (storage) medium(s) may be utilized in accordance with the above-listed embodiments of the present invention. The non-transitory computer readable (storage) medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

As will be understood with reference to the paragraphs and the referenced drawings, provided above, various embodiments of computer-implemented methods are provided herein, some of which can be performed by various embodiments of apparatuses and systems described herein and some of which can be performed according to instructions stored in non-transitory computer-readable storage media described herein. Still, some embodiments of computer-implemented methods provided herein can be performed by other apparatuses or systems and can be performed according to instructions stored in computer-readable storage media other than that described herein, as will become apparent to those having skill in the art with reference to the embodiments described herein. Any reference to systems and computer-readable storage media with respect to the following computer-implemented methods is provided for explanatory purposes, and is not intended to limit any of such systems and any of such non-transitory computer-readable storage media with regard to embodiments of computer-implemented methods described above. Likewise, any reference to the following computer-implemented methods with respect to systems and computer-readable storage media is provided for explanatory purposes, and is not intended to limit any of such computer-implemented methods disclosed herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The above-described processes including portions thereof can be performed by software, hardware and combinations thereof. These processes and portions thereof can be performed by computers, computer-type devices, workstations, processors, micro-processors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for determining the vital signs of an occupant in a vehicle comprising:
   transmitting, by a seat-mounted sensor unit, a signal to the occupant, and receiving, by the seat-mounted sensor unit, the signal as reflected from the occupant;
   filtering the received reflected signal by adjusting at least one frequency filter to produce a modified signal; and
   analyzing the modified signal to determine a breathing rate of the occupant and at least one of a heart rate of the occupant and a heart rate variability of the occupant,
   wherein determining the heart rate includes:
      dividing the modified signal into segments, each segment corresponding to a frequency, and
      analyzing a plurality of peaks of the segments for harmonics, including, for each peak:
         applying weight factors to each of the harmonics,
         accumulating energy from the harmonics as multiplied by the weight factors, and
         determining the peak of the plurality of peaks with the highest accumulated energy corresponding to the heart rate; and
   wherein determining the heart rate variability includes:
      determining artifacts in the modified signal,
      analyzing the modified signal for consecutive peaks between the artifacts,
      determining a portion of the modified signal with at least a predetermined number of consecutive peaks, and
      calculating heart rate variability parameters from the modified signal with at least a predetermined number of consecutive peaks.

2. The method of claim 1, wherein the signal is from Doppler radar.

3. The method of claim 1, additionally comprising:
   converting the received reflected signal to a converted signal, the received reflected signal being in an analog form and the converted signal being in a digital form, and
   the modified signal includes the converted signal.

4. The method of claim 3, wherein the signal reflected from the occupant results in a signal based at least on breathing rate harmonics.

5. The method of claim 1, additionally comprising:
   dividing the received reflected signal into a first pathway for determining the breathing rate and a second pathway for determining the heart rate, prior to the filtering of the received reflected signal.

6. The method of claim 5, wherein dividing the received reflected signal includes separating a breathing rate signal of the received reflected signal from a heart rate signal of the received reflected signal.

7. A method for determining the vital signs of an occupant in a vehicle comprising:
   transmitting a signal to the occupant and receiving the signal as reflected from the occupant;
   filtering the received reflected signal by adjusting at least one frequency filter to produce a modified signal; and
   analyzing the modified signal to determine at least one of a heart rate of the occupant and a heart rate variability of the occupant, wherein determining the heart rate includes:
dividing the modified signal into segments, each segment corresponding to a frequency, and
analyzing a plurality of peaks of the segments for harmonics, including, for each peak:
applying weight factors to each of the harmonics,
accumulating energy from the harmonics as multiplied by the weight factors, and
determining the peak of the plurality of peaks with the highest accumulated energy corresponding to the heart rate; and
wherein determining the heart rate variability includes:
determining artifacts in the modified signal,
analyzing the modified signal for consecutive peaks between the artifacts,
determining a portion of the modified signal with at least a predetermined number of consecutive peaks, and
calculating heart rate variability parameters from the modified signal with at least a predetermined number of consecutive peaks.

8. The method of claim 7, additionally comprising:
obtaining vibration data including vehicle movement data and vehicle acceleration data from at least one sensor in the vehicle; and
filtering the received reflected signal by adjusting at least one filter based on the obtained vibration data, to produce the modified signal.

9. A system for determining the vital signs of an occupant of a vehicle comprising:
a seat-mounted radar transceiver for transmitting a signal to the occupant and receiving the signal as reflected from the occupant;
a signal converter for converting the received reflected signal to a converted signal; and
a processor in electronic communication with the signal converter, the processor being programmed to:
a) filter the converted signal by adjusting at least one frequency filter to produce a modified signal, and
b) analyze the modified signal to determine at least one of a heart rate of the occupant and a heart rate variability of the occupant,
wherein determining the heart rate includes:
dividing the modified signal into segments, each segment corresponding to a frequency, and
analyzing a plurality of peaks of the segments for harmonics, including, for each peak:
applying weight factors to each of the harmonics,
accumulating energy from the harmonics as multiplied by the weight factors, and
determining the peak of the plurality of peaks with the highest accumulated energy corresponding to the heart rate; and
wherein determining the heart rate variability includes:
determining artifacts in the modified signal,
analyzing the modified signal for consecutive peaks between the artifacts,
determining a portion of the modified signal with at least a predetermined number of consecutive peaks, and
calculating heart rate variability parameters from the modified signal with at least a predetermined number of consecutive peaks.

10. The system of claim 9, additionally comprising:
a vibration detection unit for detecting vibrations local to the occupant and providing vibration data representative of the local vibrations including movement data and acceleration data of the vehicle, the vibration detection unit including an inertial measurement unit (IMU),
wherein the processor is additionally in electronic communication with the vibration detection unit, and the processor is additionally programmed to:
filter the converted signal by adjusting at least one filter based on the vibration data, to produce the modified signal.

11. The system of claim 9, wherein the signal converter includes an analog to digital converter (ADC).

12. The system of claim 9, additionally comprising: a filtration and amplification circuit in electronic communication with the seat-mounted radar transceiver and the signal converter, including a first passband pathway for determining the breathing rate and a second passband pathway for determining the heart rate.

13. The system of claim 10, wherein the seat-mounted radar transceiver, the signal converter, the processor and the vibration detection unit define a single sensor unit.

14. The system of claim 12, wherein a breathing rate signal of the received reflected signal is separated from a heart rate signal of the received reflected signal, the breathing rate signal being for the first passband pathway, and the heart rate signal being for the second passband pathway.

15. A method for detecting the presence of a vehicle occupant in a cabin of the vehicle, comprising:
transmitting, by a seat-mounted sensor unit, a signal, and receiving, by the seat-mounted sensor unit, the signal as reflected;
filtering the received reflected signal by adjusting at least one frequency filter to produce a modified signal;
analyzing the modified signal to determine the presence of at least a heart rate; and
detecting, based on the presence of at least the heart rate, the presence of the vehicle occupant in the cabin of the vehicle,
wherein determining the presence of at least the heart rate includes:
dividing the modified signal into segments, each segment corresponding to a frequency, and
analyzing a plurality of peaks of the segments for harmonics, including, for each peak:
applying weight factors to each of the harmonics,
accumulating energy from the harmonics as multiplied by the weight factors, and
determining the peak of the plurality of peaks with the highest accumulated energy corresponding to the heart rate.

16. The method for detecting the presence of the vehicle occupant in the cabin of the vehicle of claim 15,
wherein the seat-mounted sensor unit is located proximate to at least one of a vertebrae Lumbar-3 region and a vertebrae Lumbar-4 region.

17. The method for detecting the presence of the vehicle occupant in the cabin of the vehicle of claim 15,
wherein the analysis of the modified signal is to determine the presence of both the heart rate and a breathing rate; and
wherein the detection of the presence of the vehicle occupant in the cabin of the vehicle is based on the presence of both the heart rate and the breathing rate.

18. A method for determining the number of occupants in a vehicle cabin, comprising:

transmitting, by a plurality of seat-mounted sensor units, at least one signal, and receiving, by the plurality of seat-mounted sensor units, a plurality of signals as reflected;

filtering the plurality of received reflected signals by adjusting a plurality of frequency filters to produce a plurality of modified signals;

analyzing the plurality of modified signals to determine the presence of at least a heart rate for each signal of the plurality of modified signals; and determining, based on the presence of at least the heart rate for each signal of the plurality of modified signals, the number of occupants in the vehicle cabin, wherein determining the presence of at least the heart rate for each signal of the plurality of modified signals includes:

dividing the modified signal into segments, each segment corresponding to a frequency, and analyzing a plurality of peaks of the segments for harmonics, including, for each peak:

applying weight factors to each of the harmonics, accumulating energy from the harmonics as multiplied by the weight factors, and determining the peak of the plurality of peaks with the highest accumulated energy corresponding to the heart rate.

19. The method for determining the number of occupants in the vehicle cabin of claim 18, wherein each of the plurality of seat-mounted sensor units is located proximate to at least one of a vertebrae Lumbar-3 region and a vertebrae Lumbar-4 region.

20. The method for determining the number of occupants in the vehicle cabin of claim 18, wherein the analysis of the plurality of modified signals is to determine the presence of both the heart rate and a breathing rate for each signal of the plurality of modified signals; and wherein the determination of the number of occupants in the vehicle cabin is based on the presence of both the heart rate and the breathing rate for each signal of the plurality of modified signals.

* * * * *